United States Patent
Raia et al.

(10) Patent No.: US 7,128,246 B2
(45) Date of Patent: Oct. 31, 2006

(54) SLOTTED PLUNGER

(75) Inventors: Gioacchino Raia, Seefeld (DE); Susanne Wegner, Herrsching (DE)

(73) Assignee: 3M Espe AG, Seefeld (DE)

( * ) Notice: Subject to any disclaimer, the term of this patent is extended or adjusted under 35 U.S.C. 154(b) by 359 days.

(21) Appl. No.: 10/344,929

(22) PCT Filed: Aug. 9, 2001

(86) PCT No.: PCT/EP01/09211

§ 371 (c)(1),
(2), (4) Date: Jul. 23, 2003

(87) PCT Pub. No.: WO02/13718

PCT Pub. Date: Feb. 21, 2002

(65) Prior Publication Data

US 2004/0065690 A1    Apr. 8, 2004

(30) Foreign Application Priority Data

Aug. 17, 2000    (DE) .............................. 100 40 732

(51) Int. Cl.
*A61C 5/06*    (2006.01)

(52) U.S. Cl. ..................... 222/327; 222/386; 433/90; 604/218

(58) Field of Classification Search ................ 222/326, 222/327, 386; 433/90; 604/218, 222

See application file for complete search history.

(56) References Cited

U.S. PATENT DOCUMENTS

| 5,322,440 | A | | 6/1994 | Steele |
| 5,360,146 | A | * | 11/1994 | Ikushima .................... 222/386 |
| 5,624,260 | A | | 4/1997 | Wilcox et al. |
| 5,865,803 | A | | 2/1999 | Major |
| 5,893,714 | A | | 4/1999 | Arnold et al. |

FOREIGN PATENT DOCUMENTS

| DE | 3915268 | 12/1990 |
| GB | 1475430 | 6/1977 |

* cited by examiner

*Primary Examiner*—J. Casimer Jacyna
(74) *Attorney, Agent, or Firm*—Crowell & Moring LLP

(57) ABSTRACT

The invention relates to a receptacle with a plunger, which is displaceably arranged therein. The plunger comprises a plunger body with a flat face, whereby at least two encircling sealing lips are shaped onto the plunger body. Each sealing lip has slot-shaped notches at at least one location that, as soon as the plunger is inserted into the receptacle, permit a gas exchange between the inside of the receptacle and the outside atmosphere. The invention also relates to the use of the receptacle and of the plunger for storing and discharging, in particular, dental materials.

25 Claims, 1 Drawing Sheet

SLOTTED PLUNGER

BACKGROUND AND SUMMARY OF THE INVENTION

The invention relates to a slotted plunger, a receptacle containing the latter, and its use for closing receptacles containing dental material and for discharging the dental material from these receptacles.

From U.S. Pat. No. 5,129,825, a capsule for storing dental material is known, in which a plunger is displaceably arranged. For stabilizing the capsule when discharging very viscous dental material, the capsule is reinforced with exterior ribs. On one side, the interior of the capsule is sealed off by the plunger.

Plungers for sealing-off and for discharging dental material from capsules are also described in U.S. Pat. No. 5,083,921. It is stated that the plunger has the purpose of ensuring a largely complete discharge of dental material, in which case the penetrating of air is to be avoided.

U.S. Pat. No. 5,322,440 describes a receptacle for storing and discharging dental material, having a plunger which is displaceably arranged in the receptacle. An elastic sealing lip is molded to the plunger, which sealing lip has the purpose of, as it were, ensuring for a wiper blade that, when the plunger is moved forward, all dental material is discharged.

All these documents have in common that they provide devices which make it possible to largely completely discharge the masses packed into the receptacles.

In contrast, German Patent DE-C1-3915268 relates to a plug with sealing lips for the opening of a liquid receptacle disposed on a movable housing. The sealing lips have slot-shaped notches which are mutually offset by 180° on the circumference. On the one hand, the stopper prevents that liquid can flow out of the receptacle but, on the other hand, permits the unhindered flowing of air into the receptacle interior.

Because of its further development as a plug with a lid-type upper closing part, this plug is not suitable for discharging the liquid stored in the receptacle.

Finally, it was found in U.S. Pat. No. 5,624,260 that aqueous pasty dental materials are to be stored in receptacles whose material has a sufficiently high oxygen penetrability and a low water vapor penetrability. It is stressed that particularly the sealing ring, which may be mounted on the plunger, has to meet these definitions.

The parameters indicated in the document ensure that the stored dental material neither dries out nor polymerizes prematurely because, when radically hardenable dental materials are brought in contact with atmospheric oxygen, a beginning polymerization on the surface of the material is inhibited by the atmospheric oxygen.

The above-mentioned parameters for the oxygen penetrability and the water vapor penetrability, however, limit the available materials for producing plungers for the storing and discharging of dental material from cartridge-shaped receptacles.

It is therefore an object of the present invention to provide a plunger which, on the one hand, permits the discharging particularly of dental material from receptacles and, on the other hand, ensures that the characteristics of the stored material do not change during the storage process.

This object is achieved by providing a plunger and a receptacle containing this plunger and its use for the storage and for the discharge particularly of dental material, as described in the claims.

The invention has the following advantages: The presence of the sealing lips at the plunger results in a minimizing of the force to be applied during the discharge operation as a result of the reduced contact surface between the plunger and the interior wall of the receptacle.

The slot-shaped notches made in the sealing lips, on the one hand, as a result of the improved gas exchange with the surrounding atmosphere, permit a stabilization of the paste, and, on the other hand, as a result of the ventilation, facilitate the insertion of the plunger after the filling of the receptacle.

Despite the slot-shaped notches into the sealing lips, surprisingly, no mass flows out during the discharge operation by way of the face of the plunger although the plunger has no additional sealing devices in this area.

In addition, the molding of at least two sealing lips onto the plunger prevents a jamming of the plunger during the discharge operation.

The flat face ensures a uniform force transmission of from a forcer mounted on a discharge device to the plunger during the discharge operation.

The terms comprise and contain introduce non-exclusive listings of characteristics.

Plungers in the sense of the present invention are any shapes which can be displaceably inserted into a receptacle and are suitable, as a result of the displacement, to discharge the material situated in the receptacle by way of an opening from the receptacle.

In this context, the term "plunger" implies a sufficiently tight edge closure between the exterior surface of the plunger and the interior wall of the receptacle at least in the area in which the plunger is displaceable.

In the present case, this edge closure is achieved predominantly by the presence of sealing lips which are, for example, molded onto the plunger body.

In principle, the plunger may have any shape but preferably has a cylindrical or barrel-shaped construction. A shape with a cylindrical basic body to which a truncated cone is molded is also contemplated.

The term "barrel-shaped" applies to all geometrical shapes whose front and end area have a smaller circular section than the center area, in which case the cross-sectional change may take place continuously or in steps. Shapes are therefore also included which are obtained by joining two truncated cones to a cylinder. In this case, the two molded-on truncated cones must not necessarily have identical dimensions.

The angle of slope of the optionally molded-on truncated cones is normally in the range of from 70° to 88°, preferably in the range of from 80° to approximately 85°. The height of these truncated cones is normally in the range of from 0.3 mm to 2.0 mm, preferably in the range of from 0.5 mm to 1.5 mm.

A sufficiently tight edge closure means that it is ensured that, when the plunger moves forward, the material disposed in the receptacle, during the discharge operation, does not flow out against the forward movement over the face of the plunger.

The flat face of the plunger is the surface onto which pressure is normally exercised by means of a forcer which moves the plunger forward in the receptacle. This surface normally corresponds essentially to the interior cross-sectional surface of the receptacle at the point at which the plunger is introduced into the receptacle. The face is essentially oriented at a right angle with respect to the interior wall of the receptacle.

The term "receptacle" comprises any geometrical shape with an internal volume, the internal volume predominantly having a shape into which a plunger can be displaceably inserted. The internal volume preferably has a cylindrical shape.

The receptacles have a forward and a rearward opening, the ratio of the diameter of the forward opening to the rearward opening preferably being in the range of from 1:10 to 1:2, particularly in the range of from 1:8 to 1:5. The forward opening normally has a nozzle-type shape with a preferably constant inside diameter.

The forward opening of the receptacle is optionally provided with a cap or a displacement stopper which has a coding, preferably a color. It was found to be advantageous to dye this area to the color of the mass to be discharged.

In the dental field, such receptacles are normally called "computes" and have a volume in the range of from 0.1 to 2 cm$^3$, preferably in the range of from 0.2 to 1.5 cm$^3$.

Sealing lips are moldings onto the, or indentations at the, plunger which are to ensure a sufficiently tight edge closure between the plunger and the interior wall of the receptacle.

A cross-sectional shape of the sealing lips is preferable which ensures a minimal contact surface between the sealing lip and the interior surface of the receptacle. Here, wedge-shaped cross-sectional shapes were found to be advantageous which lead into a narrow plateau surface, the wedge-shaped tapering onto the plateau surface taking place from both sides of the sealing lip, but preferably only from one side.

The wedge-shaped areas normally have a slope in the range of from 20° to 50°, preferably in the range of approximately 30° to 40°.

It is particularly preferable for the sealing lip closest to the front surface to first rise perpendicularly in the cross-section, extend over a plateau surface and then drop off in a wedge-shape.

The following possibilities exist for the forming-on of the sealing lips: After the manufacturing of the central plunger body, the sealing lips may, for example, be shaped on by gluing or shrinking on.

Preferably, the sealing lips are molded to the central plunger body during the manufacturing of the plunger, particularly by injection molding through recesses in the injection mold die onto the central plunger body.

However, it is also possible to subsequently process the plunger by cutting methods, such as milling or shaving, in which case the sealing lips can be worked out by the removal of material.

The sealing lips are preferably made of a flexible material which facilitates the adaptation to unevennesses of the interior surface of the receptacle.

In this case, the outside diameter of the plunger measured in the area of the sealing lips is normally slightly larger than the inside diameter of the receptacle in order to ensure a uniformly narrow contacting of the contact surfaces.

The term "slot-shaped notches" comprises all interruptions in the sealing lip which prevent a tight edge closure between the sealing lip and the interior wall of the receptacle in this area. These may be notches, indentations or recesses.

Pasty masses are, for example, materials whose viscosity is such that, for discharging the mass from a small special steel tube (length 20 mm, diameter 2 mm) half filled with the mass, an average force in the range of from 20N to 300 N, preferably 50N to 150 N, has to be exercised upon a massive plunger.

Such masses are sufficiently stable so that they do not dissolve under their own force of gravity on a surface. These masses can be plastically deformed only under the effect of exterior pressure and can be pressed through an opening.

Examples of such masses in the dental field are particularly dental filler materials, such as composites, compomers and pasty glasionomer cements.

In the receptacles according to the invention, masses are preferably stored which are largely anhydrous and/or contain only constituents not easily volatilized under normal conditions.

The term "pasty masses" comprises all hardenable materials on an acrylate and/or epoxy resin base.

The ratio of the length of the plunger to the diameter averaged along the plunger length is normally in the range of from 1:1 to 2:1, preferably in the range of from 1.5:1 to 1.7:1. The plunger normally has a total length of from 3 mm to 15 mm, preferably from 5 mm to 10 mm.

The spacing of the at least two sealing lips with respect to one another is normally in the range of from 1 mm to 7 mm, preferably in the range of from 2 mm to 5 mm.

The plunger may optionally also have three, four or five sealing lips. The sealing lips are preferably uniformly distributed along the length of the plunger.

It was found to be advantageous for the plunger body to have a barrel-shaped construction. This facilitates the introducing of the plunger into the receptacle.

The discharge force to be applied, that is, the force which has to be applied in order to discharge the pasty mass from the receptacle, depends particularly on the following factors:

The viscosity of the mass to be discharged, the volume quantity of the mass to be discharged, the cross-section of the forward opening of the receptacle, the inside diameter of the receptacle in the area of the displaceable plunger, and the curvature radius or geometry during the transition from the cylindrical interior of the receptacle to the forward outlet opening.

With the number of the slot-shaped notches existing in the sealing lips, the gas exchange of the receptacle interior with the outside atmosphere is improved. Sealing lips with two, three or four slot-shaped notches respectively were found to be particularly advantageous when, on the one hand, a sufficient gas exchange is to be ensured and, on the other hand, the plunger has to still sufficiently seal off the receptacle toward the rearward opening. However, optionally, more than four slot-shaped notches may also be present in the sealing lip.

The danger of a flowing-out of mass to be discharged over the face of the plunger during the discharge operation can be additionally reduced if the slot-shaped notches of one sealing lip are arranged to be offset by 180° with respect to the slot-shaped notches of the other sealing lip.

An adaptation of the shape of the front face of the plunger to the face of the interior of the receptacle permits a largely complete discharge of the mass. Conical, step-shaped or oval front faces were found to be advantageous here.

If a largely optimal force transmission from the forcer, which presses on the face of the plunger, to the mass contained in the receptacle is to be ensured, it is advantageous when the front face of the plunger has a largely flat construction and the cross-sectional surface corresponds essentially to the inside diameter of the receptacle at its inlet opening.

The plunger and the receptacle are preferably manufactured from injection-moldable materials, such as PE, PP, POM, PA, PET, PBT, PTFE or fluoric polyolefines or mixtures of these polymers.

The material is preferably adapted to the mass to be stored in the receptacle or to the monomers contained therein. Nonpolar polyolefines are used when the diffusion of polar monomers from the mass to be stored into the receptacle or the plunger or through the receptacle is to be prevented. Polar polyolefines are preferably used for storing masses which contain nonpolar volatile constituents.

It may also be advantageous to coat the plunger with substances improving the sliding characteristics, such as fluoridated polyolefines, or to manufacture the plunger and/or the receptacle from these materials.

The face of the plunger can also be marked in color in order to facilitate the identification of the mass situated in the receptacle.

After the filling with the pasty mass to be stored and to be discharged, the receptacle according to the invention, for the use, is preferably placed in a pistol-type discharge device (for example, FIG. 1 of U.S. Pat. No. 5,083,921). During the discharge, force is in this case transmitted by way of a forcer of the discharge device to the face of the plunger, which leads to a forward movement of the plunger in the receptacle interior and to a displacement of the pasty mass through the forward opening of the receptacle.

Preferred embodiments are explained in detail in the following by means of the drawings.

DETAILED DESCRIPTION OF THE DRAWINGS

Figure 1:
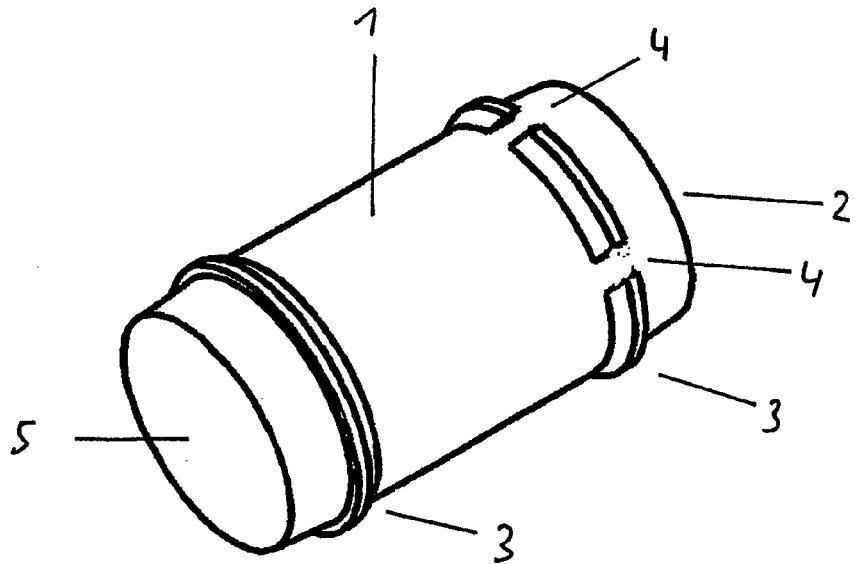
FIG. 1 is a perspective view of the plunger.

According to FIG. 1, the plunger comprises a central plunger body (1), a flat face (2) on which the forcer of a discharge device can be placed, two sealing lips (3) with two slot-shaped notches (4) respectively. The slot-shaped notches of the one sealing lip are arranged to be offset with respect to the slot-shaped notches of the second sealing lip.

Figure 2:
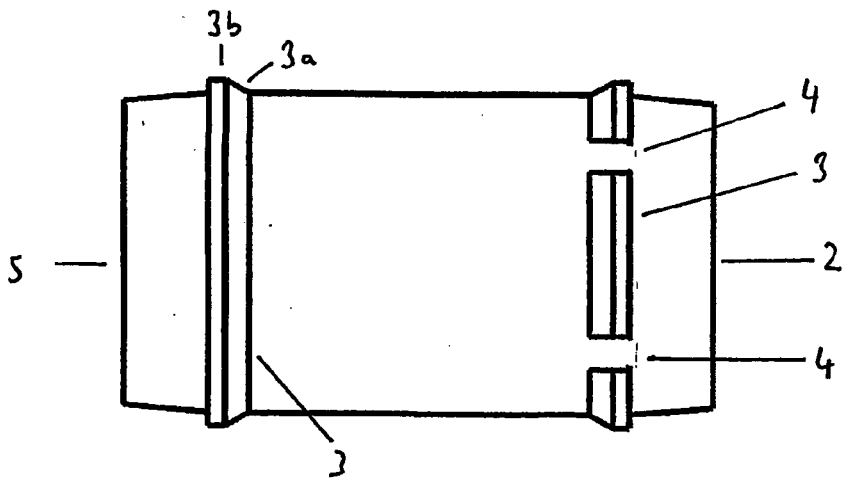
FIG. 2 is a lateral view of the plunger.

FIG. 2 is a cross-sectional view of the plunger, the wedge shape (3a) of the sealing lips (3) being shown which leads into a plateau surface (3b). Also outlined is the barrel-shaped construction of the plunger body which, in the present case, is formed of a forward and a rearward truncated cone and of a center cylinder.

Figure 3:
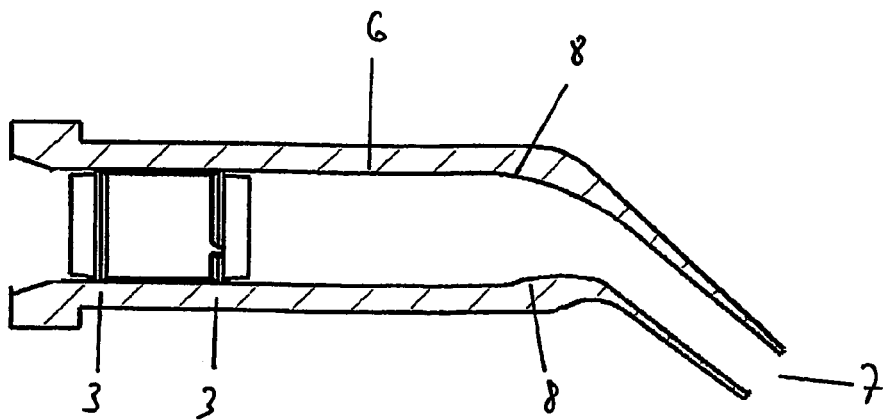
FIG. 3 is a view of a receptacle according to the invention containing the plunger.

FIG. 3 is a view of an example of a receptacle according to the invention, as it is customary in the dental field for storing and for discharging filling materials. In the present case, the piston contacts the interior wall (6) of the receptacle only by way of the sealing lips (3). Since the piston has no additional sealing elements in the area of the face, a sufficient gas exchange is ensured between the interior of the receptacle and the surrounding atmosphere.

LIST OF REFERENCE NUMERALS

1 plunger body
2 face
3 sealing lip
3a wedge-shaped area
3b plateau-shaped area
4 slot-shaped notch
5 front face
6 interior wall of the receptacle
7 forward opening of the receptacle
8 face of the interior

The invention claimed is:

1. Plunger, for use in a receptacle for holding material to be discharged having flat front and rear faces with a discharge opening on the front face, comprising a plunger body having a rear flat face and a front flat face, wherein the rear face and the front face of the plunger largely correspond to the interior of the receptacle front and rear faces, and wherein the plunger body comprises at least two surrounding sealing lips which each have slot-shaped notches at least at one point, which notches permit a gas exchange between the receptacle interior and the outside atmosphere as soon as the plunger has moved into a fitting receptacle.

2. Plunger according to claim 1, wherein the plunger body has a barrel-shaped construction.

3. Plunger according to claim 1, wherein the sealing lips each have two slot-shaped notches.

4. Plunger according to claim 2, wherein the sealing lips each have two slot-shaped notches.

5. Plunger according to claim 1, wherein the slot-shaped notch or notches of one sealing lip are arranged offset to the slot-shaped notch or notches of the other sealing lip.

6. Plunger according to claim 2, wherein the slot-shaped notch or notches of one sealing lip are arranged offset to the slot-shaped notch or notches of the other sealing lip.

7. Plunger according to claim 3, wherein the slot-shaped notch or notches of one sealing lip are arranged offset to the slot-shaped notch or notches of the other sealing lip.

8. Plunger according to claim 4, wherein the slot-shaped notch or notches of one sealing lip are arranged offset to the slot-shaped notch or notches of the other sealing lip.

9. Plunger according to claim 1, wherein the front face of the plunger has a cross-sectional surface that corresponds essentially to the inside diameter of the receptacle.

10. Plunger according to claim 2, wherein the front face of the plunger has a cross-sectional surface that corresponds essentially to the inside diameter of the receptacle.

11. Plunger according to claim 3, wherein the front face of the plunger has a cross-sectional surface that corresponds essentially to the inside diameter of the receptacle.

12. Plunger according to claim 5, wherein the front face of the plunger has a cross-sectional surface that corresponds essentially to the inside diameter of the receptacle.

13. A method for closing receptacles containing pasty masses and discharging the masses from these receptacles wherein the receptacles have flat front and rear faces with a discharge opening on the front face comprising inserting a plunger body into the receptacle, wherein the plunger body has a rear flat face, a front flat face, wherein the rear face and the front face of the plunger largely correspond to an interior of the receptacle, and wherein the plunger body has at least two surrounding sealing lips which each have slot-shaped notches at least at one point, and wherein the notches permit a gas exchange between the receptacle interior and the outside atmosphere.

14. Method according to claim 13, wherein the receptacle has a predominantly cylindrical interior.

15. Method according to claim 13, wherein the plunger body has a barrel-shaped construction.

16. Method according to claim 13, wherein the sealing lips each have two slot-shaped notches.

17. Method according to claim 13, wherein the slot-shaped notch or notches of one sealing lip are arranged offset to the slot-shaped notch or notches of the other sealing lip.

18. Method according to claim 13, wherein the front face of the plunger has a cross-sectional surface that corresponds essentially to the inside diameter of the receptacle.

19. Receptacle having a flat front face, an outlet on the front face and a plunger displaceably disposed therein which comprises a plunger body having a rear flat face and a front flat face, wherein the flat front face faces the outlet, wherein the plunger body comprises at least two surrounding sealing lips, each sealing lip having a slot-shaped notch at least at one point, and which, as soon as the plunger is moved into the receptacle, permit a gas exchange of the receptacle interior with the outside atmosphere.

20. Receptacle according to claim 19, containing a dental material.

21. Receptacle according to claim 20, wherein the dental material is selected from pasty glasionomer cements, composites, or compomers.

22. A dental material dispensing assembly including:
a receptacle for pasty dental material, and
a plunger slideably disposable in the receptacle to forceably push the dental material out of the receptacle, said plunger including:
a plunger body with a flat forcer engaging face at a rear end thereof which in use is opposite a flat face at a front end thereof engageable with the dental material and wherein the front face of the plunger body largely corresponds with a face of an interior of the receptacle, and
at least two axially spaced sealing lips surrounding the plunger body and adapted in use to engage interior surface sections of the receptacle,
wherein each of said sealing lips have at least one slot shaped axially extending recess which in use permits gas exchange between the interior of the receptacle which in use contains the dental material and surrounding atmosphere.

23. A dispenser assembly according to claim 22, wherein the dental material is selected from pasty glasionomer cements, composites, or compomers.

24. A dispenser assembly according to claim 22, wherein the sealing lips each have two slot-shaped notches.

25. A dispenser assembly according to claim 24, wherein the slot-shaped notch or notches of one sealing lip are arranged offset to the slot-shaped notch or notches of the other sealing lip.

* * * * *

UNITED STATES PATENT AND TRADEMARK OFFICE
CERTIFICATE OF CORRECTION

PATENT NO.         : 7,128,246 B2  
APPLICATION NO. : 10/344929  
DATED                 : October 31, 2006  
INVENTOR(S)       : Gioacchino Raia et al.

It is certified that error appears in the above-identified patent and that said Letters Patent is hereby corrected as shown below:

Column 2,  
Line 8, delete "paste," and insert in place therefor --paste--.  
Line 18, delete "of" after "transmission".

Column 3,  
Line 15, delete ""computes"" and insert in place thereof --"compules"--.

Signed and Sealed this

Twentieth Day of May, 2008

JON W. DUDAS  
*Director of the United States Patent and Trademark Office*